United States Patent
Salcedo et al.

(10) Patent No.: US 10,584,151 B2
(45) Date of Patent: Mar. 10, 2020

(54) RECOMBINANT PEPTIDE VACCINES AGAINST TICKS, AND NUCLEOTIDE SEQUENCES CODING FOR THE RECOMBINANT PEPTIDES

(71) Applicants: FUNDACAO DE AMPARO A PESQUISA DO ESTADO DE MINAS GERAIS-FAPEMIG, Belo Horizonte (BR); UNIVERSIDADE FEDERAL DE VICOSA, Vicosa (BR); PATSOS INDUSTRIA E COMERCIO DE PRODUTOS BIOTECHNOLOGICOS LTDA, Viscosa (BR)

(72) Inventors: Joaquin Hernan Patarroyo Salcedo, Vicosa (BR); Marlene Isabel Vargas Viloria, Vicosa (BR); Sidimar Sossal, Viscosa (BR); Leandro Silva de Araujo, Vicosa (BR); Gabriel Andres Tafur Gomez, Viscosa (BR); Marcio Alberto Dias Mendes, Vicosa (BR)

(73) Assignees: Fundaçao de Amparo a Pesquisa do Estado de Minas Gerais-Fapemig, Belo Horizonte (BR); Universidade Federal de Vicosa, Vicosa (BR); Patsos Industria e Comercio de Produtos Biotecnológicos LTDA, Vicosa (BR)

( * ) Notice: Subject to any disclaimer, the term of this patent is extended or adjusted under 35 U.S.C. 154(b) by 0 days.

(21) Appl. No.: 15/029,982

(22) PCT Filed: Oct. 15, 2014

(86) PCT No.: PCT/BR2014/000371
§ 371 (c)(1),
(2) Date: Apr. 15, 2016

(87) PCT Pub. No.: WO2015/054764
PCT Pub. Date: Apr. 23, 2015

(65) Prior Publication Data
US 2016/0237127 A1    Aug. 18, 2016

(30) Foreign Application Priority Data
Oct. 16, 2013  (BR) .......................... 102013026625

(51) Int. Cl.
*C07K 14/435*   (2006.01)
*A61K 39/00*    (2006.01)

(52) U.S. Cl.
CPC .... *C07K 14/43527* (2013.01); *A61K 39/0003* (2013.01); *A61K 2039/53* (2013.01); *A61K 2039/552* (2013.01)

(58) Field of Classification Search
None
See application file for complete search history.

(56) References Cited

U.S. PATENT DOCUMENTS

2016/0237127 A1* 8/2016 Salcedo ............. A61K 39/0003

FOREIGN PATENT DOCUMENTS

| BR | 9300625 A | 10/1994 |
|----|-----------|---------|
| BR | PI 9300625-0 A | 10/1994 |
| BR | 0001717 A | 3/2002 |
| WO | 8803929 A1 | 6/1988 |

OTHER PUBLICATIONS

Medeiros, C L "Vacina de DNA utilizando genes sinteticos derivados do peptideo SBm7462 contra o carrapato Rhipicephalus (Boophilus) microplus e avaliacao da resposta imune em camundongos Balb/c". Dissertacao de Mestrado apresentada a Universidade Federal de Vicosa, Vicosa (MG), UFV, 2008.
Patarroyo, J H et al. "Immunization of cattle with synthetic peptides derived from the Boophilus microplus gut protein (Bm86)", Vet. Immunol. Immunopathol., vol. 88, No. 3-4, 2002, pp. 163-172. ISSN: 0165-2427.
Rand, K N et al. "Cloning and expression of a protective antigen from the cattle tick *Boophilus microplus*", Proc. Natl. Acad. Sci. USA, vol. 86, No. 24, 1989, pp. 9657-9661.
Arthur, Ticks and disease London: Pergamon Press, 1961. 150p.
Holroyd et al., Australian Journal Experimental Agriculture 28: p. 1-10, 1987.
Branco et al., Coletãnea de Pesquisa EMBRAPA, p. 229-234, 1987.
Furlong et al., XV Congresso Panamericano De Ciências Veterinárias. Campo Grande PRCA: p. 340.
Jonsson et al., Veterinary Parasitology 78: 65-77, 1998.
Horn and Arteche, A Hora Veterinária. 4:12-32, 1985.
Grissi et al., A Hora veteranária. 21:8-10, 2002.
Freire, Boletim da Direção de Produção Anual. 9:3-31, 1953.
Freire, Boletim da Direção de Produção Anual. 13:62-80, 1956.
Shaw et al., Journal Economic Entomology 61:1590-1594, 1968.
Amaral et al., Journal Economic Entomology 67:387-389. 1974.
Wharton, Wild Animal Review. 20:8-15, 1976.

(Continued)

*Primary Examiner* — Nita M. Minnifield
(74) *Attorney, Agent, or Firm* — Jason P. Mueller; Adams and Reese LLP

(57) ABSTRACT

The present invention relates to the field of biotechnology and genetic engineering, and particularly to the expression of recombinant peptides. The inoculation thereof in cattle results in the production of an immune response capable of adversely affecting *Rhipicephalus microplus* ticks, which feed on the inoculated cattle, decreasing the number and reproductive capacity of this tick species. Such recombinant immunogen can be used as an effective vaccine for tick control. The technical goal is the design and construction of two synthetic genes made with preferred codons for *Pichia pastoris* and expression thereof from a recombinant peptide, which consists in a continuous sequence and of a recombinant peptide, respectively, and the drug composition based of said recombinant polypeptide.

1 Claim, 2 Drawing Sheets

Specification includes a Sequence Listing.

(56) References Cited

OTHER PUBLICATIONS

Patarroyo and Costa, Tropical Health Animal Production 12:6-10, 1980.
Oliveira et al., Arquivos Brasileiros de Mecicina Veteranária e Zootecnia. 38:205-214, 1986.
Flausino et al., Revista Brasileira de Parasitologia Veterinária. 4:45, supplement 1, 1995.
Martins E Furlong, Veterinary Record 149:64, 2001.
Labruna and Veríssimo, Arquivos Instituto Biológico 68:115-120, 2001; Ruvalcaba Fernandez et al., Experimental and Applied. Acarology. 32: 293-299, 2004.
Ruvalcaba Fernandez et al., Experimental and Applied. Acarology. 32: 293-299, 2004.
Heimerdinger et al., Journal of Veterinary Parasitology. 15:37-39, 200; Broglio-Micheletti et al., Revista Brasileira de Parasitologia Veterinária. 18:44-48, 2009.
Broglio-Micheletti et al., Revista Brasileira de Parasitologia Veterinária. 18:44-48, 2009.
Andreotti, Embrapa Gado de Corte, Didactic Article 2002.
Samish and Glazer, Trends Parasitology. 17:368-371, 2001.
Vasconcelos et al., Parasitology Research. 94:201-206, 2004.
Jonsson et al., Veterinary Parasitology, 89:297-305, 2000.
Frisch et al., International Journal for Parasitology. 30:253-264, 2000.
Veríssimo et al., Arquivos do Instituto Biológico. 71:630-632, 2004.
Jonsson, Veterinary Parasitology. 137:1-10, 2006.
Dalton and Mulcahy, Veterinary Parasitology.98: 149-167 2001.
Smith et al., The development of TickGard a commercial vaccine against the cattle tick *Boophilus microplus*. Indooroopilly: Biotec Autralia—CSIRO, 17 p. 1995.
Willadsen, Veterinary Parasitology. 71:209-222 1997.
García-García et al., Vaccine 16:1053-1055, 1998.
Rodriguez et al., Journal of Biotechnology 33:135-143, 1994.
Jonsson et. al, Veterinary Parasitology. 88:275-285, 2000.
García-García et al., Vaccine. 18:2275-2287, 2000.
García-García et al., Experimental and Applied Acarology. 23:883-895 1999.
Patarroyo et al., Veterinary Parasitology 166:333-339, 2009.
Sossai et al., Experimental and Applied Acarology 37:199-214 2005.
Peconick et al., Experimental Parasitology 119:37-43, 2008.
Nuttall et al., Parasite Immunology. 28:155-163 2006.
OBA Revista da Faculdade de Veterinária e Zootecnia da Universidade de São Paulo 13: 409-420 1976.
Massard et al., Revista Brasileira de Medicina Veterinária 17:167-173, 1995.
Medeiros, Vacina de DNA ultilizando genes sintéticos derivados de peptídeo SBm7462 contra o carrapato Rhipicephalus (Boophilus) microplus e avaliação da resposta imune em camundongos Balb/c. Dissertação de Mestrado apresentada à Universidade Federal de Vicosa (MG), UFV, 2008.
Patarroyo et al., Immunization of cattle with synthetic peptides derived from the Boophilus microplus gut protein (Bm86), Vet. Immunol. Immunopathol., vol. 88, No. 3-4, 2002, p. 163-172. ISSN:0165-2427.
Rand et al., Cloning and expression of a protective antigen from the cattle tick *Boophilus microplus*, Proc. Natl. Acad. Sci. USA, V.86, No. 24, 1989, p. 9657-9661. ISSN: 0027-8424.

* cited by examiner

SEQUENCE LISTING

```
<160> NUMBER OF SEQ ID NOS: 6

<210> SEQ ID NO 1
<211> LENGTH: 438
<212> TYPE: DNA
<213> ORGANISM: Artificial Sequence
<220> FEATURE:
<223> OTHER INFORMATION: synthetic gene designed for transfection in
      Pichia pastoris and tandem production of the amino acid sequence

<400> SEQUENCE: 1
ctcgaggaaa agaagagaga agcagaagct tgtcttagca agcatgttct aaggaagtta      60
caagcttgcg aacactgtga ttgtggagaa tggggagcta tgaacatgac gacaagatca     120
tcgatttgct cagatttcgg taacgagttt tgcagaaacg cttgtttgtc caagcatgtc     180
ttgaggaagt tgcaagcttg tgaacactgt gattgtggtg aatggggtgc tatgaacatg     240
acaaccagat cctctatatg ctctgatttc ggtaacgagt tttgtaggaa cgcatgcctt     300
tctaagcatg tccttagaaa gcttcaagca tgtgagcatt gtgactgtgg agaatggggt     360
```

```
gcaatgaaca tgactactag atccagtatc tgttccgatt tcggaaacga attttgtaga      420
aacgcttgtt aagaattc                                                   438
```

<210> SEQ ID NO 2
<211> LENGTH: 171
<212> TYPE: DNA
<213> ORGANISM: Artificial Sequence
<220> FEATURE:
<223> OTHER INFORMATION: synthetic gene designed for transfection in
      Pichia pastoris and tandem production of the amino acid sequence

<400> SEQUENCE: 2

```
ctcgaggaaa agagagaagc agaagcttgt cttagcaagc atgttctaag gaagttacaa      60
gcttgcgaac actgtgattg tggagaatgg ggagctatga acatgacgac aagatcatcg     120
atttgctcag atttcggtaa cgagttttgc agaaacgctt gttaagaatt c              171
```

<210> SEQ ID NO 3
<211> LENGTH: 145
<212> TYPE: PRT
<213> ORGANISM: Artificial Sequence
<220> FEATURE:
<223> OTHER INFORMATION: Sequence of non-consecutive amino acids
      originating from intestinal protein of Rhipicephalus microplus,
      repeated in tandem

<400> SEQUENCE: 3

```
Leu Glu Glu Lys Lys Arg Glu Ala Glu Ala Cys Leu Ser Lys His Val
1               5                   10                  15

Leu Arg Lys Leu Gln Ala Cys Glu His Cys Asp Cys Gly Glu Trp Gly
            20                  25                  30

Ala Met Asn Met Thr Thr Arg Ser Ser Ile Cys Ser Asp Phe Gly Asn
        35                  40                  45

Glu Phe Cys Arg Asn Ala Cys Leu Ser Lys His Val Leu Arg Lys Leu
    50                  55                  60

Gln Ala Cys Glu His Cys Asp Cys Gly Glu Trp Gly Ala Met Asn Met
65                  70                  75                  80

Thr Thr Arg Ser Ser Ile Cys Ser Asp Phe Gly Asn Glu Phe Cys Arg
                85                  90                  95

Asn Ala Cys Leu Ser Lys His Val Leu Arg Lys Leu Gln Ala Cys Glu
            100                 105                 110

His Cys Asp Cys Gly Glu Trp Gly Ala Met Asn Met Thr Thr Arg Ser
        115                 120                 125

Ser Ile Cys Ser Asp Phe Gly Asn Glu Phe Cys Arg Asn Ala Cys Glu
    130                 135                 140

Phe
145
```

<210> SEQ ID NO 4
<211> LENGTH: 56
<212> TYPE: PRT
<213> ORGANISM: Artificial Sequence
<220> FEATURE:
<223> OTHER INFORMATION: Sequence of non-consecutive amino acids
      originating from intestinal protein of Rhipicephalus microplus.

<400> SEQUENCE: 4

```
Leu Glu Glu Lys Arg Glu Ala Glu Ala Cys Leu Ser Lys His Val Leu
1               5                   10                  15

Arg Lys Leu Gln Ala Cys Glu His His Asp Cys Gly Glu Trp Gly Ala
```

```
                20                  25                  30
Met Asp Met Thr Thr Arg Ser Ser Ile Cys Ser Asp Phe Gly Asn Glu
                    35                  40                  45

Phe Cys Arg Asn Ala Cys Glu Phe
        50                  55

<210> SEQ ID NO 5
<211> LENGTH: 21
<212> TYPE: DNA
<213> ORGANISM: Artificial Sequence
<220> FEATURE:
<223> OTHER INFORMATION: primers 5-prime AOX1

<400> SEQUENCE: 5
gactggttcc aattgacaag c                                          21

<210> SEQ ID NO 6
<211> LENGTH: 21
<212> TYPE: DNA
<213> ORGANISM: Artificial Sequence
<220> FEATURE:
<223> OTHER INFORMATION: primers 3-prime AOX1

<400> SEQUENCE: 6
gcaaatggca ttctgacatc c                                          21
```

RECOMBINANT PEPTIDE VACCINES AGAINST TICKS, AND NUCLEOTIDE SEQUENCES CODING FOR THE RECOMBINANT PEPTIDES

CROSS-REFERENCE TO RELATED APPLICATIONS

This application is the National Stage entry of International Application No. PCT/BR2014/000371, filed Mar. 25, 2014, which claims benefit of Brazilian Priority Application to BR 102013026625-6, filed Oct. 16, 2013, both of which are incorporated in their entirety by reference thereto.

FIELD OF THE INVENTION

This invention relates to the field of biotechnology and genetic engineering, and particularly to the expression of recombinant peptides. The inoculation of these in cattle results in the production of an immune response capable of adversely affecting *Rhipicephalus microplus* ticks, which feed on the inoculated cattle, decreasing the number and reproductive capacity of this tick species. Such recombinant immunogen can be used as an effective vaccine for tick control.

The first object of this patent application is related to two nucleotide sequences encoding two recombinant peptides. The second object of this patent application is related to the amino acids sequences that comprise the recombinant peptide. The third object of this application is related to two different presentations of a recombinant peptides based vaccine against ticks, containing the recombinant peptides produced in *Pichia pastoris*, saponin added as adjuvant. The nucleotide sequences, recombinant peptides, and vaccines described herein may be used in the immunization of animals in cattle parasite tick control programs, and represent alternatives to vaccines available on the market. These products mentioned above may be used in pharmaceutical industries or animal health field.

STATE OF PRIOR ART

The common tick of cattle, belonging to the Ixodidae family, is the main ectoparasite of cattle in Brazil and in all tropical and subtropical countries. It is an extremely well-adapted parasite to the climate conditions of most part of the country, and together with the presence of their hosts distributed in more than 90% of the country, it is a problem of major proportions to Brazilian cattle. The associated losses are not limited only to the production drop due to the intense haematophagy but also to other damages such as the effect of parasite saliva in the bovine immune system, leather depreciation, influence on the production capacity of animals and, especially, transmission of several microorganisms that cause diseases of importance in national livestock such as *Babesia bovis* and *Babesia bigemina*, with participation in the epidemiology of anaplasmosis caused by *Anaplasma marginate*.

The direct damage caused by the intense haematophagy conducted, mainly, by females, reaching an amount of 0.6 to 3 mL per teleoginae (ARTHUR, Ticks and disease London: Pergamon Press, 1961. 150p), reflects on production loss. HOLROYD et al., (Australian Journal Experimental Agriculture 28: p. 1-10, 1987) observed that animals that did not have contact with ticks had gains averaged over 17 kg in three years, when compared to those who were exposed to the parasite. In Brazil, BRANCO et al., (Coletânea de Pesquisa EMBRAPA), p. 229-234, 1987) found average weight gain of 34.5 Kg in cattle of Hereford breed. In 1996 FURLONG et al., (XV CONGRESSO PANAMERICANO DE CIÊNCIAS VETERINÁRIAS. Campo Grande PRCA: p. 340) observed a small decline in milk production in growing and successive infestations. JONSSON et al., (Veterinary Parasitology 78: 65-77, 1998), in Australia, estimated that each teleoginae (adult female) would be responsible for the daily production loss of 8.9 mL of milk and 1.0 g of body weight.

It should also be count as losses to Brazilian cattle expenditures related to the direct control of the ticks and the diseases transmitted by it. HORN and ARTECHE (A Hora Veterinária. 4:12-32, 1985) estimated in 800 million dollars the direct and indirect losses. The Ministry of Agriculture, in work done in the biennium 1983/1984, raises this value to US$1 billion figure, being that 40% of this amount is related to losses in milk production.

Taking into account the data calculated in 1985 Grissi et al., (A Hora veteranária. 21:8-10, 2002) updated the caused losses coming to the figure of US$2 billion year; of course this calculation includes direct and indirect damages, including transmitted diseases. Therefore, what could be called the complex *Rhipicephalus microplus*/hematozoa, would give an average annual loss of US$11.76 per bovine. Currently, the cattle population in the country is estimated at 200 million head, which theoretically would reach R$2.3 billion annually.

The control method most used worldwide is the chemical, based on acaricides (pesticides) of different bases. However, implications of various orders have been noted, especially the development of resistance by ticks by the active ingredients employed. Moreover, the constant use of these products, given the resistance, has led to contamination of ecosystems and to the presence of waste in food derived from animal origin. Thinking on foreign meat and milk market, it must undergo sanitary barriers on residues in meat and milk, and derivatives thereof. Recently, occurred the embargo of tons of meat products by macrocyclic lactones waste used as endectocides.

In Brazil, according to FREIRE (Boletim da Direção de Produção Anual. 9:3-31, 1953), the resistance to arsenic was first documented in 1950. This same researcher (Boletim da Direção de Produção Anual. 13:62-80, 1956) reported the first cases of resistance to chlorinated compounds occurring in Rio Grande do Sul estate. The resistance to organophosphates in Brazil was described by SHAW et al., (Journal Economic Entomology 61:1590-1594, 1968); AMARAL et al., (Journal Economic Entomology 67:387-389. 1974): WHARTON (Wild Animal Review. 20:8-15, 1976); PATARROYO AND COSTA (Tropical Health Animal Production 12:6-10, 1980) and Oliveira et al., (Arquivos Brasileiros de Medicina Veterinária e Zootecnia. 38:205-214, 1986). FLAUSINO et al., (Revista Brasileira de Parasitologia Veterinária. 4:45, supplement 1, 1995), working in the state of Rio de Janeiro, showed the resistance factors regarding the LD50 for the chemical base amitraz as 50.7 and ranging from 8.5 to 20.9 regarding alphamethrin pyrethroids, deltamethrin and lambda (λ) cyhalothrin. The same researchers in the country's northeast region, and specifically in the state of Pernambuco, found resistance to compounds, which have amidine as chemical basis and to the synthetic pyrethroids cypermetrina and deltamethrin. MARTINS E FURLONG (Veterinary Record 149:64, 2001) studying Brazilian samples of *R. microplus*, found resistance to moxidectin, doramectin and ivermectin, which indicantes the emergence of cross-resistance to the chemical group of avermectins. Such publications show that all chemical bases existing in the market has caused resistance in populations of this parasite, being necessary to increase the dosage of the product or to increase the frequency in the treatment, increasing the contamination.

Worldwide, there are several lines of research for alternative methods for *R. microplus* tick control. Alternative control measures are proposed as a way of minimize obstacles arising from the use of chemical fungicidal, which, in addition to resistance, bring waste problems for animal products and to the environment.

Among these alternative measures, it can be highlighted the use of pastures, or the rotational use of them, which hinder larvae access or that release volatile agents (LABRUNA and VERÍSSIMO, Arquivos Instituto Biológico 68:115-120, 2001; RUVALCABA FERNANDEZ et al., Experimental and Applied. Acarology. 32: 293-299, 2004). Another measure that has been addressed is the bath of animals with herbal extracts that inhibit the larvae access (Heimerdinger et al., Journal of Veterinary Parasitology. 15:37-39, 200; BROGLIO-MICHELETTI et al., Revista Brasileira de Parasitologia Veterinária. 18:44-48, 2009). The entomoparasitas employment is another technique under evaluation. Among the entomoparasitas, it can be highlighted the *Megaselia scalaris* fly which reduces the number of eggs of teleoginae (ANDREOTTI, Embrapa Gado de Corte, Didactic Article 2002). Entomopathogenic nematodes are promising biological agents in the control of several tick species, including *R. microplus*, destroying the hemocele of these species (Samish and Glazer, Trends Parasitology. 17:368-371, 2001; Vasconcelos et al., Parasitology Research. 94:201-206, 2004).

The animal breeding in the selection of more resistant strains to tick is still a controversial process. There is controversy over estimates of heritability values and it has been questioned the correlation between the tick resistance trait and the animal productivity (JONSSON et al., Veterinary Parasitology, 89:297-305, 2000; FRISCH et al., International Journal for Parasitology. 30:253-264, 2000). What is known is that cattle with higher levels of zebu blood (*Bos indicus*) have greater resistance to parasites, and, even within this group, there are races differences. The Nellore cattle, for example, are more resistant than the Gir or Guzerá (Verissimo et al., Arquivos do Instituto Biológico. 71:630-632, 2004; JONSSON, Veterinary Parasitology. 137:1-10, 2006).

Despite ongoing research concerning non-polluting and non-chemical alternatives to tick control, yet very little is known about the ecological interactions and the impact that the introduction of alien species, whether vertebrate or invertebrate, cause the environment. Pending a final solution in this field, the alternative left to the producer is still the use of acaricide drugs, however the problems of their employment, briefly reported previously, lead to a reality that urges the discovery and development of an fighting alternative to this parasite.

Research and scientific advances in immunology, as the growing understanding of biology of parasites, use of modern tools such as molecular biology, and high production scale allow antiparasitic vaccines to be a great possibility (DALTON and MULCAHY, Veterinary Parasitology. 98: 149-167 2001). The development of vaccines against ticks is a clear alternative of control.

The identification of protective antigens for bovine against *R. microplus* is increasing, regarded the economic impact and the difficulties already mentioned, in the control of this parasite.

In 1994, in Australia, it was released the first commercial vaccine against *R. microplus* using the gene bm86 cloning in Escherichia coli and the production of the recombinant protein Bm86 (rBm 86), given the name TickGARD® (Hoechst Animal Health, Australia), and subsequently named TickGARD Plus® (Smith et al., The development of TickGard a commercial vaccine against the cattle tick *Boophilus microplus*. Indooroopilly: Biotec Autralia-CSIRO, 17 p. 1995; Willadsen, Veterinary Parasitology. 71:209-222 1997). With the bases of the same antigen, the vaccine Gavac® was formulated in Cuba (Heber Biotec S.A., Havana, Cuba) and Gavac Plus®, but this rBm 86 was produced in *Pichia pastoris* (GARCÍA-GARCÍA et al., Vaccine 16:1053-1055, 1998).

The efficacy of these vaccines has varied between 50 and 91%. These values are evaluated by viability reduction and the number of eggs, consequently reducing the number of ticks in subsequent generations, having committed all the development stages (RODRIGUEZ et al., Journal of Biotechnology 33:135-143, 1994; JONSSON et. al, Veterinary Parasitology. 88:275-285, 2000).

Some samples of *R. microplus*, however, were less susceptible to the recombinant vaccine Bm86 (rBm86). The inefficiency was determined in an Argentine population later named as strain A, which showed that it had a different gene, the bm95 gene, which was then cloned and expressed in *P. pastoris* yeast and used as another recombinant vaccine controlling the population that was resistant to rBm86 (Garcia-Garcia et al., Vaccine. 18:2275-2287, 2000).

The geographic isolation of *R. microplus* strains can lead to these genetic and physiological differences, referring to a negative response to the control by vaccination (GARCÍA-GARCÍA et al., Experimental and Applied Acarology. 23:883-895 1999). Thus, there is a constant search for an immunogen, or combination of antigens, that covers the largest possible number of populations, protecting the flock from infestations by *R. microplus*.

The patent document WO2012041260 deals with the control of ectoparasites and transmitted diseases. They are several sequences of ribosomal proteins (POs) that form chimeras with different proteins. With respect to ticks, and specifically to *R. microplus*, the full-length protein called Bm86 was used as an antigen eliminating the gene fragments of the signal peptide and the transmembrane region to construct a chimeric protein (Bm86-pPO). It was inoculated in cattle using the Montanide as an adjuvant. It has no similarity to the current application for patenting because it is not the recombinant peptide and the claims have no similarity to our demands.

In the patent document WO2009127766, are used peptides of the protein called Bm95 of the *R. microplus* to be fused to the N-terminal region of the surface protein called MSPla of *Anaplasma marginate*. It is not similar to this application, it is not a recombinant peptide expressed by transfection of synthetic genes in yeast for the bovine common tick control, the *R. microplus*.

The patent document ZA9901320 is related to the biotechnology field of vaccines, i.e. to the development of peptide vaccines (Mimotopes) to control the cattle tick. Said vaccine has potential application due to the fact that the tick proteins are recognized by sera from mice inoculated with the peptide fused-phages that express, and also by the fact that teleoginae ticks had a blackish color suggesting hemorrhagic damage in challenge tests. Given that, there is a great need for new methods for controlling *Rhipicephalus microplus*, a potential vaccine can be developed using isolated peptides, together or associate with existing antigen, for effective control of tick. For the above, it was used the technique of phage display, which is very wide and selects many possible peptides with the possibility of being used because is a mapping. Said process consists of repeated cycles of selection, the eluted wash, and the amplification of filamentous phage, which express the random peptide sequences that bind with affinity for several molecules, including immunoglobulins. It has no similarity to our request for patenting because it is not a single recombinant peptide expressed by transfection of synthetic genes with proven action to control *R. microplus* on cattle.

The Patent document CA1339466 of tick vaccine, specifically of *R. microplus*, refers to the gene encoding the protein named Bm86, which is composed by 650 amino acids. The protein can be found in natural state in such tick and has not undergone any change because it is the protein found naturally in the parasite. It is not similar to the current application due to it is a full length protein and is different from this request because it refers to a recombinant peptide produced by transfection of synthetic genes in *P. pastoris* yeast strain KM71.

The patent document PI 0001717-5, AU 779 537, MX 270 574, EN 1289545, ES 236043, U.S. Pat. No. 8,110,202 present a synthetic vaccine for the control of *Rhipicephalus (B.) microplus*. It has been shown that the developed vaccine elicits a complete immune response to any antigen complex. It is interesting to note that the vaccine stimulates a T-dependent immune response. (Patarroyo et al., Veterinary Parasitology 166:333-339, 2009).

Genetic variability studies analyzing 20 samples of different places and geographical conditions of Brazilian regions, and other South American countries, have shown that the patented sequence SBm7462 remained conserved among all populations (SOSSAI et al., Experimental and Applied Acarology 37:199-214 2005; PECONICK et al., Experimental Parasitology 119:37-43, 2008), concluding that there is not variability in these sequences that may interfere with the vaccine efficiency. This reinforced the concept of universal antigen or immunogen. It also means that the antigenic determinants of the developed vaccine are present in all studied populations.

The SBm7462 synthetic vaccine controls efficiently *R. microplus*, however it presents limitations for producing the synthetic peptide in large scales.

Taking into account the needs to control the parasite and the efficiency of the developed immunogen SBm7462, it is needed an alternative mean to produce the same. Thus, a new way of producing the same was developed from the fermentation by transfection of synthetic genes of yeast that would encode the synthetic peptide.

Through recombinant DNA techniques, the vaccine can be produced more efficiently (lower cost, shorter time and large-scale production) being effective for Brazil ticks, as well as develop a non-toxic product, without waste, and which does not impact adversely the environment.

The action of the vaccine upon application to the herd works as follows: the proteins are inoculated in cattle and they induce the reaction of the body defense system, which creates specific antibodies against the protein. Parasitizing the vaccinated animal, the ticks suck the blood containing antibodies against its own intestinal cells. The result is an intestinal destruction, which kills the ticks or, at least, reduces their ability to adequately feed and reproduce.

When applying the vaccine antigens, the cattle develop a protective immunity against ticks, which will prevent many direct and indirect damages that may be caused by this mite. The vaccines based on recombinant antigens do not present a health risk, are safe for the environment, and the development of resistance by ticks through selective adaptation is unlikely (NUTTALL et al., Parasite Immunology. 28:155-163 2006).

Among the advantages of using this vaccine, to the detriment of acaricide, it can be highlighted: no grace period after application, since it does not leave residues in food, crucial factor in milk cattle; more sustainable action, they are environmentally friendly, since they are nontoxic to the animal, to the environment, and to humans; do not destroy the natural microflora, because it is species-specific will only reach the ticks of the species *R. (B.) microplus* without attacking natural microorganisms inherent in the cattle; and development of resistance by ticks by selective adaptation is unlikely.

The developed recombinant DNA vaccine is suitable for ticks *R. (B.) microplus* found in Brazil and other South American countries. Genetic variability studies analyzing 20 samples of ticks from different places and geographical conditions of Brazilian regions and Argentina, Venezuela, Colombia, and Uruguay confirm the presence of antigenic epitopes in these populations (SOSSAI et al., Experimental and Applied Acarology. 37:199-214, 2005; PECONICK et al., Experimental Parasitology 119:37-43, 2008).

The vaccine developed is a herd vaccine in which vaccinating the herd for three annual cycles decreases the tick population, which leads to minimizing the above-mentioned losses and avoid the use of 19 or 20 Acaricide, as it is currently being done in many farms of the country.

This invention has high social and environmental impact because, currently, there is the need to meet consumer demands for food free of chemicals, protection of the environment, and, consequently, the wild animals. Thus, in a market where the products to combat ectoparasites are mainly chemicals, it is necessary to invest in research and manufacture of alternative products for the control of these agents.

The vaccines are safe, have a good interface with the environment, and are more readily accepted by consumers, perhaps by the familiarity they have with the vaccine used in human medicine. With its use, there is a greater production and animal productivity increasing than the use of other medications.

The vaccine, by being subunits (it is not a full length protein) and immunologically defined, do not contain remains of organisms different to the amino acid sequence comprising the recombinant peptide, making it safe to animals and the environment.

The development of vaccines to combat ticks, or ectoparasites in general, becomes relevant especially by not leaving residues in animal products (meat and milk) and not harming the environment, because their formulations do not have chemicals compounds such as antibiotics and/or heavy metals, among others.

Contrary to the vaccines, the chemicals used today for combating ticks are highly toxic. If cattle are treated with acaricide and the grace period is not respected, meat and milk should not be intended for human consumption because they are subject to the risk of poisoning, which, for prolonged periods, can lead to harmful effects on human being.

DETAILED DESCRIPTION OF THE INVENTION

Obtaining Encoding Sequences

Figure 1:
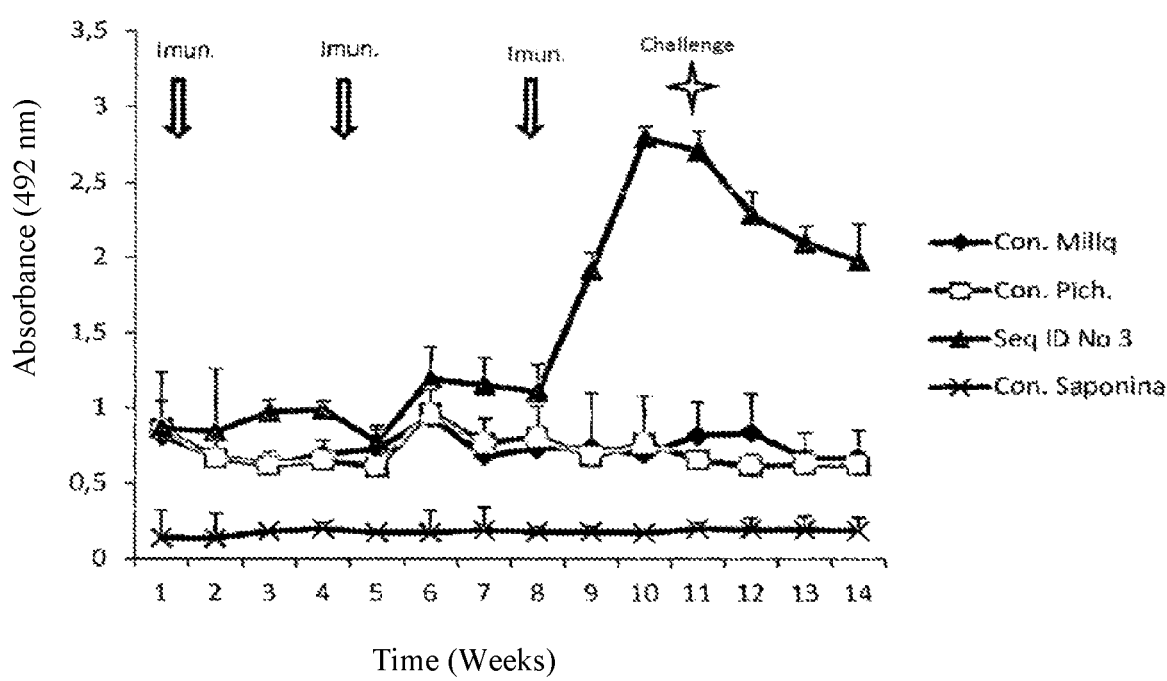
FIG. 1—Kinetics of antibodies in animals immunized with SEQ ID NO. 3. The arrows indicate inoculation and the star the time of challenge with larvae of *Rhipicephalus* (*B.*) *microplus*. The T bars indicate the difference by the adding of a standard deviation.

Two genes called seq1 (SEQ ID NO: 1) and seq4 (SEQ ID NO: 2) were designed from the reverse vaccinology methodology using as base the synthetic peptide on the SBm7462 for use in *P. pastoris* yeast km71. The seq4 gene was constructed in order to express a similar copy of SBm7462. However, the seq1 gene was designed to express the peptide repeated three times in tandem. The genes were designed with preferred codons for *P. pastoris*. For the genes drawings, the cloning sites of the expression vector used were taken into consideration. The vector used has an insertion region of heterologous fragments composed of several restriction sites for enzymes called (XhoI, SnaBI, EcoRI, AvrII and NotI).

Construction of Expression Cassettes seq1 (SEQ ID NO: 1) and seq4 (SEQ ID NO: 2)

The sequences corresponding to the genes were cloned into the pPIC9 vector, which was subjected to cleavage with appropriate restriction enzymes. Through these divisions, sticky ends were formed on both vectors and genes, allowing the connection of the genes in the correct ORFs (Open Reading Frame) in their respective expression vectors. All cleavage reactions were analyzed by agarose gel electrophoresis 0.8%. The construction of the cassettes were given through the use of the enzyme $T_4$DNA ligase, whose function was to catalyze the bonding of the cohesive ends of the strands 5'-3' of the vector with the 3'-5' of the gene and vice versa.

Analyses of the Expression Cassettes by Colony PCR and Sequencing.

The constructed expression cassettes were multiplied in *E. coli* DH5a. Clones of each gene were analyzed by colony PCR and subsequently sequenced in order to verify the correct presence of the gene in the expression cassette.

The clones confirmed by sequencing were subjected to growth in LB liquid medium at 37° C., under 250 rpm orbital shaking for 16 hours for subsequent extraction of the expression cassettes that were used to transform the yeast *Pichia pastoris* KM71.

Preparations of Cassettes seq1 (SEQ ID NO: 1) and seq4 (SEQ ID NO: 2) for Electroporation.

For the transformation of *P. pastoris* km71 by electroporation, the expression cassettes were linearized with restriction enzyme Scl (WU and LETCHWORTH, Drug Discovery and Genomic Technologies, 36:152-154, 2004).

In each cleavage reaction, it was used approximately 20 μg of plasmid DNA in excess of three times the enzyme at 37° C. and overnight.

The monitoring of the cleavage was carried out before the end of the reaction by gel electrophoresis in 1% agarose, stained with ethidium bromide, and visualization under UV light. After verification of the total linearization of the expression cassettes, the entire reaction was applied in adjacent channels on 0.8% agarose gel and subjected to electrophoresis. The extraction of the bands containing the linearized plasmid was given using appropriate commercial kit. The extracted material was subsequently precipitated with ethanol in order to concentrate it to 10 μg in 10 uL of nuclease-free water, which was the final volume used in the transformation of the yeast.

*P. pastoris* Km71 Yeast Transformations with the Expression Cassettes and Selection in MD Medium.

The genetic transformation of the yeast *P. pastoris* km71 occurred by electroporation technique. To this, 10 g of each plasmid previously linearized with the restriction enzyme were added to 80 μL of electronically competent cells and transferred to 0.2 cm electroporation cuvettes. The DNA and *P. pastoris* km71 mixture was kept on ice for 5 minutes to allow thermal equilibration of the solution. After this period, the cuvettes were placed in electroporation cell and subjected to an electrical pulse (1.5 kV, 25 μg, and 200Ω).

Immediately after electroporation, 1 mL of sorbitol 1M was added in the electroporation chamber and kept in the ice bath for 5 minutes. After this period, 200 μL of the transformants were plated on MD solid medium lacking histidine (YNB 1.34%, biotin $4\times10^{-5}$%, dextrose 2% and bacteriological agar 1.5%). For all transformed clones, plating were made in duplicates. The plates were maintained at 30° C. for 72 hours until complete growth of the clones. The selection with the MD medium is due because only the yeasts transformed with the vector pPIC9 develop due to the presence of the histidinol dehydrogenase gene that synthesizes the amino acid histidine.

Confirmations of *P. pastoris* Km71 Clones by Polymerase Chain Reaction (PCR).

Besides the selection of transformed clones of *P. pastoris* Km71 by the passage in medium lacking histidine (MD), clones of each gene were subjected to the extraction of total DNA and amplification thereof by PCR.

The chromosomal DNA of the previously selected clones was extracted from cultures grown in liquid MD under 250 rpm stirring for 48 hours at 30° C. The culture was recovered by centrifugation, for 10 minutes, at 5000 g at room temperature. The pellet was resuspended in 400 μL of extraction solution (Triton 100× 2%, SDS 1%, NaCl 100 mM, Tris-HCl 100 mM and EDTA 10 mM, pH 8.0), and transferred to a 2 mL tube containing 300 mg of glass beads of 0.45 mm in diameter used for mechanical lysis of the yeast through orbital shaking vigorously for 2 minutes. Subsequently, 200 μL of phenol and 200 μL of chloroform were added and again proceeded to vigorous shaking for two minutes to enhance lysis of cells and subsequent DNA extraction. After this phase, the solution was centrifuged for 5 minutes at 5000 g. The aqueous phase was transferred to a new tube and treated with RNAse (10 μL of a 10 mg/mL solution) for 1 hour at 37° C. and, right after, with proteinase K (20 μL of a 10 mg/mL solution) for 2 hours at 37° C. The precipitation was performed by adding 1/10 volume of sodium acetate pH 5.2, plus 2 volumes of cold absolute ethyl alcohol. The solution was gently stirred and kept at −20° C. for two hours to increase the yield of DNA precipitation and then centrifuged for 5 minutes at 5000 g. The pellet was washed with 70% ethanol for two successive centrifugations and dried at room temperature. Subsequently, the DNA was re-suspended in 100 μL of nuclease-free water, quantified in agarose gel 1% with lambda DNA, and stored at −20° C. until use.

To determine the insertions of the genes in yeast chromosome it was used the PCR technique and the primers 5'AOX1 (5'-GACTGGTTCCAATTGACAAGC-3') [SEQ ID NO: 5] and 3'AOX1 (5'-GCAAATGGCATTCTGACATCC-3') [SEQ ID NO: 6].

Selections of seq1 (SEQ ID NO: 1) and seq4 (SEQ ID NO: 2) Clones by Colony Blotting.

The *P. pastoris* Km71 clones preselected through MD and PCR for recombinant expression were selected by protein production analysis by Western Blotting colony. The technique was chosen because the yeasts transformed with the cassette SEQ ID NO: 1 and SEQ ID NO: 2 export the expressed protein into the extracellular medium. For that, clones transformed with SEQ ID NO: 1 and SEQ ID NO: 2 were selected randomly. These two clones were plated on petri dishes containing the solid YPD medium until the colonies reach a mean diameter of 3 mm, in an oven at 30° C. Once reaching the required size with the aid of a nitrocellulose membrane, the clones were collected and transferred by imprint and passed to other two of MM expression medium containing plates (YNB 1.34%, biotin $4 \times 10^{-5}$%, methanol 0.5% and bacteriological agar 1.5%) with a 0.2 μm nitrocellulose membrane equilibrated in this medium at 30° C. for 12 hours. The imprints were placed in direct contact with the 0.2 μm membranes, taking care to remove all air between the membranes. The plates were incubated at 30° C. for 72 hours, necessary time to have an optimum proteins expression and their transfer to the membrane.

After the genes induction period, the nitrocellulose membranes were collected so to avoid the drag of the colonies as much as possible. Subsequently, the nitrocellulose membranes were treated with methanol 100% for 1 minute to fix the protein and immediately subjected to 3 successive washings, 20 seconds each, with Milli-Q water.

The detection of producing clones was performed by enzyme immunoassay dot-blotting. Thereunto, the membranes were blocked with PBST 0.05% pH 7.6 (NaCl 4.25 g; $Na_2HPO_4$ 0.64 g; $NaH_2PO_4 \cdot H_2O$ 0.068 g; Tween-20 0.05% and $H_2O$ Milli-Q q.s.p. 500 mL) for 30 minutes under side agitation. After this step, the membranes were subjected to three successive washes with PBST 0.05% for 5 minutes each and, then, incubated for two hours with anti-synthetic peptide rabbit serum SBm7462 diluted at 1:100 (positive control) and the other with normal rabbit serum, or not immunized with the synthetic peptide SBm7462, diluted at 1:100 (negative control). Immediately after the incubation, the membranes were again subjected to three washes of 5 minutes each with PBST 0.05% and then incubated with peroxidase labeled protein A diluted at 1:400 for 1 hour.

The development of the reaction took place after two washes of 5 minutes each with PBST 0.05% and once with PBS pH 7.6. The substrate was formulated with 10 mg of DAB (diaminobenzidine), 10 mL of Tris-HCl 0.05M pH 7.6; 1 mL of $NiCl_2$ 0.3% and 10 μL of $H_2O_2$ 30%. The solution was stirred together with the membranes until the early appearance of the background on the negative control. At this time, the reaction was stopped by washing the membrane with Milli-Q water.

Stability Evaluation of the Recombinant Clones

To evaluate the genetic stability of the recombinants, they were transferred to YPD agar (yeast extract 10 g/L, peptone 20 g/L, glucose 20 g/L, bacteriological agar 20 g/L) and incubated at 30° C. until the appearance of isolated colonies. Thereafter, five colonies of each transformant were successively transferred to non-selective complete medium, YPD, with a total of ten passes. Each pass through the plates were incubated at 30° C. for 72 hours. At the end of the fifth passage, the colonies were transferred to selective MD medium lacking histidine and incubated at 30° C. for a further 72 hours.

Production of Peptides in Bench Fermenter

Pre-Inoculum:

A *P. pastoris* clone, frozen with glycerol, at a culture-glycerol ratio of 70%/30%, kept in ultrafreezer (−70° C.), is thawed on ice and grown in 500 mL erlernmeyer containing 250 mL of Medium B (Table 1) at 30° C., and orbital agitation of 250 rpm for 2 days. The sterility of the biomass was examined by light microscopy.

TABLE 1

Composition of Part B.

| | Amount used for 1 L |
|---|---|
| $KH_2PO_4$ | 13 g |
| $(NH_4)_2SO_4$ | 8.75 g |
| $MgSO_4$ | 4.5 g |
| $CaCl_2 \cdot 2H_2O$ | 0.5 g |
| Yeast extract | 2.5 g |
| Glycerol | 40 mL | pH 5.0. Must be autoclaved.

Fermentation:

The production of recombinant antigen on a laboratory scale is carried out by fermentative processes in a bioreactor. To the pre-inoculum, 21 mL of PTM1 Trace Salts (Table 2) and 1 mL of antifoam are added. This mixture is placed in a sterile flask with cannula adapted to the bioreactor and added to the 4.5 L of sterile medium B already in the reactor through positive pressure. The reactor is then turned on and the parameters are maintained constant: 2 mmHg oxygen continuous injection, 600 rpm rotation and water jacket maintained at 30° C. The pH is maintained between 5 and 5.5, adjusted with ammonium hydroxide 50% or phosphoric acid 50% diluted in autoclaved water. The buffer are kept in separate flasks connected to the peristaltic pump, which is programmed for automatic pH correction.

TABLE 2

Composition of PTM1* Medium.

| | Amount used for 1 L |
|---|---|
| $CuSO_4 \cdot 5H_2O$ | 6 g |
| NaI | 0.08 g |
| $MnSO_4 \cdot H_2O$ | 3 g |
| $Na_2MoO_4 \cdot 2H_2O$ | 0.2 g |
| Boric Acid | 0.02 g |
| $CoCl_2$ | 0.5 g |
| $ZnCl_2$ | 20 g |
| $FeSO_4 \cdot 7H_2O$ | 65 g |
| Biotin | 0.2 g |
| Sulfuric acid | 5 mL |

*must be filtered

Feeding

As the oxygen parameters dissolved in the medium are monitored, and taking into account that the oxygen levels remained low for the consumption, during the biomass growth and multiplication phase, when it rises reaching around 90%, which is approximately 2 days after the start of the fermentation, 400 mL of a sterile solution is added to the medium containing glycerol 50% in water and 6 mL of PTM1/L. After that, dissolved oxygen values should fall again, indicating return to their consumption and multiplication.

Induction

When all source of carbon provided (glycerol) have been exhausted, the dissolved oxygen parameter will further increase which occurs approximately 3 days after feeding.

At this point, begins the induction of the recombinant peptide production with pure methanol, in that a final volume of 400 mL of methanol is added to the culture for 4 days at 1-hour intervals. In the first two hours, a volume of approximately 2 mL is added to the culture adaptation to the new carbon source and, from the 3rd hour, about 4 mL/h, and remains so until the end of the total volume. It is also added separately 1 ml of PTM1 daily.

Purification

[01] After the induction period, the culture is centrifuged at 4° C. for 15 minutes at 4500 rpm. The supernatant is then subjected to cross-flow filtration, first being clarified in 100 kDa filter, form which the permeable, i.e., the content weight lower than 100 kDa, is collected and subjected to new filtration in 30 kDa filter, where again all permeable is collected. The filtration product is subjected, by the same tangential filtration system, to a dialysis with milli-Q water chilled to 4° C. The sterilization of the product is done by filtration through 0.45 μm membrane and collected in sterile flasks. The sterilization tests are done by inoculating in Sabureau medium and blood agar maintained in bacteriological greenhouse at 37° C. for 96 hours.

Subsequently, the protein is measured to quantify the dose and packaged in polyurethane flasks, and stored under refrigeration at 4° C.

The recombinant peptides identified as SEQ ID NO: 3 and SEQ ID NO: 4, encoded by SEQ ID NO: 1 and SEQ ID NO: 2, respectively, were used as immunogens to the *Rhipicephalus* (*B.*) *microplus* tick control.

Demonstration Experiment

Efficiency Evaluation of Recombinant Immunogens SEQ ID NO: 3 and SEQ ID NO: 4

20 crossbred male cattle were used (H/Z), blood average 7/8, between 6 and 10 months old, coming from dairy farms in the County of Vicosa, MG estate, and maintained since its birth in the arthropod vectors proof cattle isolation.

The animals were identified by numbered earrings. The feeding was based on balanced feed and forage (hay) with 17% protein, offered at 8 am and 4 pm and water ad libitum.

The animals were randomly distributed into four groups of 04 animals each. The inoculations were performed in three doses, subcutaneously, as follows:

First inoculation: day 0 (zero);
Second inoculation: day 30;
Third inoculation: day 60.

The inoculation scheme is described below:

Group SEQ ID NO: 3: saponin 1.5 mg added to recombinant peptide 1 mg diluted in 4 mL of sterile Milli-Q water.

Group SEQ ID NO: 4: saponin 1.5 mg added to recombinant peptide 2 mg diluted in 4 mL of sterile Milli-Q water.

Saponin adjuvant control group: saponin 1.5 mg diluted in 4 mL of sterile Milli-Q water.

Control Group: 4 mL of sterile Milli-Q water.

*Pichia pastoris* Group: crude extract of *P. pastoris* not transfected 2 mg diluted in 4 mL of sterile milli-Q water.

The inoculated animals were constantly monitored, twice a day, for seven days after inoculation for verification of possible hypersensitivity skin reactions to recombinant peptides and adjuvant; besides the daily visual inspection, hematocrit tests were performed on all animals on the seven days after inoculation to observe some hemolytic effect of the recombinant peptides.

Challenge and Infestation of the Cattle

After 21 days of the last inoculation of the recombinant peptides, all animals were challenged with larvae of *R.* (*B.*) *microplus*, in the amount of 1,500 larvae per day for three days, beginning in the morning.

Day 1—breast and dewlap regions
Day 2—scapular and between the forelimbs regions
Day 3—scrotal and inguinal regions The animals were kept in halter and tied by the tail for 8 hours in order to correct fixation of the larvae.

Biological Parameters Evaluation of the detached teleoginae

After the challenge with tick larvae, daily observations were performed until the eighteenth day to check the development of the larvae, nymphs, and predict the likely beginning day of the detachment of teleoginae from the animals. At 21 days, with the beginning of the females fall, it was initiated the collecting procedure, manually, for all teleoginae found on the floor of the stalls, in the feeding trough, and in the grid for debris flow. For a more accurate collection, the bay was washed two times a day and, throughout this wash, the resulting material was sieved, and the removed teleoginae ticks were counted and identified.

Number of Teleoginae

It was recorded the naturally detached teleoginae as well as the trampled.

Weight of Teleoginae

The female collected were washed in running water and weighed in analytical balance with a precision of 3 decimal places in order to determine the percentage of reduction of their average weight.

Posture Weight

After weighing, the females collected were individually wrapped and identified, and left in oviposition for two weeks in an oven at 27° C. and 80% relative humidity (OBA Revista da Faculdade de Veterinária e Zootecnia da Universidade de São Paulo 13: 409-420 1976). After the end of posture, the total posture weight of each group was evaluated.

Larva Weight/Eggs Gram Ratio

From the total eggs, twenty aliquots of 0.5 g (10,000 eggs) per group were separated in centrifuge tubes, making a total of 10 grams of eggs per group. The tubes were stoppered with cotton wool and the eggs incubated for 26 days in a 28° C. greenhouse and 80% relative humidity. Aliquots were taken at more than one day of eggs weighing. To obtain the results, the techniques described above were employed by (MASSARD et al., Revista Brasileira de Medicina Veterinária 17:167-173, 1995).

Formulas for the Biological Parameters Evaluation

In order to evaluate the effect of immunogens on the biological parameters of the tick, were employed the formulas advocated by DE LA FUENTE (Recombinant Vaccines for the control of cattle tick Habana: ELPOS Scientae, p. 280, 1995) used for vaccine groups and the control groups, as follows:

$$DT\ (\%)=100[1-(NTV/NTC)]$$

wherein:

DT (%)—Reduction percentage in the number of teleoginae
NTV—number of teleoginae for each vaccination group
NTC—number of teleoginae for control group.

$$DR\ (\%)=100[1-(PMTV/PMTC)]$$

wherein:

DR (%)—Reduction percentage in the average weight of teleoginae

PMTV—Average weight of teleoginae for each vaccine group;

PMTC—Average weight of teleoginae for control group.

$$DO\ (\%) = 100[1-(PMOV/PMOC)]$$

wherein:

DO (%)—Reduction percentage of average weight of the eggs.

PMOV—Average weight of the eggs for each vaccine group.

PMOC—Average weight of the eggs for control group.

$$DF\ (\%) = 100[1-(PPLOV/PPLOC)]$$

wherein:

DF (%)—Reduction in the eggs fertility.

PPLOV—Average weight of larvae per gram of eggs in each vaccine group.

PPLOC—Average weight of larvae per gram of eggs in the control group.

$$EF\ (\%) = 100[1-(CRT \times CRO \times CRF)]$$

wherein:

EF (%)—Immunogen effectiveness.

CRT—Reduction in the number of adult females (1−DT)

CRO—Reduction in the oviposition capacity (1−DO)

CRF—Reduction in fertility (1−DF)

The values obtained for each vaccine group were statistically analyzed by Tukey test.

Humoral Kinetic Studies

The blood collection of animals was done weekly from week 0 to week 14, and the first sample was collected before the first inoculation. The serum obtained from each sample was aliquoted into Eppendorf tubes at −20° C. The kinetics were measured using enzyme immunoassay ELISA.

The Maxisorp® plate were coated with a carbonate buffer solution of pH 9.6 ($Na_2CO_3$ 0.159 g; $NaHCO_3$ 0.293 g, $H_2O$ Milli-Q q.s.p. 100 mL), wherein the peptide was diluted in the amount of 2 mg/well, leaving to adsorb at 4° C. overnight. After this period, the plates were washed twice with Wash Buffer solution (NaCl 9.0 g; Tween-20 0.5 mL, $H_2O$ dd q.s.p. 1000 mL) and added to the blocking solution—Casein 2% in PBS pH 7 6 (NaCl 4.25 g; $Na_2HPO_4$ 0.64 g; $Na_2HPO_4.H_2O$ 0.068 g, $H_2O$ Milli-Q q.s.p. 500 mL) for one hour at room temperature. The plates were washed twice and thereafter 100 mL/well of the experimental animals sera was added diluted at 1:100 in Incubation Buffer solution (PBS 87.5 mL pH 7.6, 12.5 mL Casein 2% in PBS pH 7.6; Tween 20 50 mL) and allowed to incubate for two hours at room temperature. The plates were washed six times with wash buffer solution and proceeded with incubation for two hours at room temperature, of the secondary antibody—IgG rabbit anti-IgG bovine conjugated to peroxidase, diluted in incubation buffer solution, the volume of 100 mL/well. The plates were washed six times with wash buffer and added to the developing solution at 100 mL/well of volume comprised of Substrate Buffer 20 mL ($Na_2HPO_4$ 7.19 g, citric acid 5.19 g, and $H_2O$ Milli-Q q.s.p. 1000 mL), O.P.D. 4 mg (q-phenyldiaminebenzene) and $H_2O_2$ 2.5 mL, for a period of 20 minutes in the dark. The reaction was stopped with 30 mL/well of sulfuric acid 1:20. The reading was performed on ELISA reader at 492 nm.

To discriminate the cut point between positive and negative for antibody response measured in ELISA, it was used the addition of two standard deviations from the negative controls.

Statistical Analysis

It was used the analysis of variance (ANOVA) to compare the various tests. For this, it was found that the data met the assumptions of normality and variance of the samples, and thus, the Tukey test was done.

All statistical analysis were performed using the statistical software Sigmastat® Version 2006.

Results

The data set for the biological parameters analyzed after counting and weighing teleoginae, weighing eggs and larvae, as well as the reducing parameters of the number and weight of the teleoginae, the egg weight, fertility and efficiency are shown in Table 3. It can be seen that the number of adult ticks (teleoginae) detached from the control group was higher than in the groups immunized with the recombinant peptides, SEQ ID NO: 3 and SEQ ID NO: 4, showing a lower number unfastened form immunized groups, being the reductions statistically significant when compared to the controls, and, also, statistically different reducing of engorged female ticks from animals immunized with the two recombinant peptides. It may also be observed that the detached teleoginae, both from the control group and the immunized with recombinant peptides obtained from the sequences, showed no statistically significant differences between them with respect to the average weight.

By analyzing the average weight of the eggs, it was found that there was no statistically significant difference between the different control groups with each other nor compared these with the results for the group of animals immunized with the recombinant peptide SEQ ID NO: 4; however when comparing the results of the various controls with those obtained in the group of animals immunized with the recombinant peptide SEQ ID NO: 3 they were significantly lower showing statistical difference, there were also statistically significant results among groups of animals immunized being the average weight of the eggs lower in the group immunized with the recombinant peptide SEQ ID NO: 3.

TABLE 3

Biological parameters of *Rhipicephalus* (B.) *microplus* from animals immunized with the recombinant peptides SEQ ID NO: 4 and SEQ ID NO: 3 and control groups of *P. pastoris*, adjuvant control, Milli-Q water control. The different letters (a, b, c) indicate a statistically significant difference at 0.01% level of significance in Tukey test.

| BIOLOGICAL PARAMETERS GROUPS | | | | | |
|---|---|---|---|---|---|
| | *Pichia* Control | Saponin Control | Milli-Q Control | SEQ ID NO: 4 | SEQ ID NO: 3 |
| Number of teleoginae detached | $1049^a$ | $1046^a$ | $1055^a$ | $362^c$ | $522^b$ |
| Average weight of teleoginae detached | $0.2553^a$ | $0.2541^a$ | $0.2558^a$ | $0.2516^a$ | $0.2404^b$ |
| Average weight of oviposition | $0.1224^a$ | $0.1380^a$ | $0.1290^a$ | $0.1183^a$ | $0.0901^b$ |
| Larva weight/gram of eggs | $0.0533^a$ | $0.0528^a$ | $0.0557^a$ | $0.0441^b$ | $0.0102^c$ |

TABLE 3-continued

Biological parameters of *Rhipicephalus* (B.) *microplus* from animals immunized
with the recombinant peptides SEQ ID NO: 4 and SEQ ID NO: 3 and control groups of
*P. pastoris*, adjuvant control, Milli-Q water control. The different letters (a, b, c)
indicate a statistically significant difference at 0.01% level of significance in Tukey test.

BIOLOGICAL PARAMETERS GROUPS

|  | Pichia Control | Saponin Control | Milli-Q Control | SEQ ID NO: 4 | SEQ ID NO: 3 |
|---|---|---|---|---|---|
| Weight of eggs reduction (OF) |  |  |  | 3.35%[a] | 26.38%[b] |
| teleoginae reduction (DT) |  |  |  | 65.49%[a] | 50.23%[b] |
| Fertility reduction (DF) |  |  |  | 17.26%[a] | 80.86%[b] |
| Effectiveness (EF) |  |  |  | 72.56% | 92.99%[b] |

Figure 2:
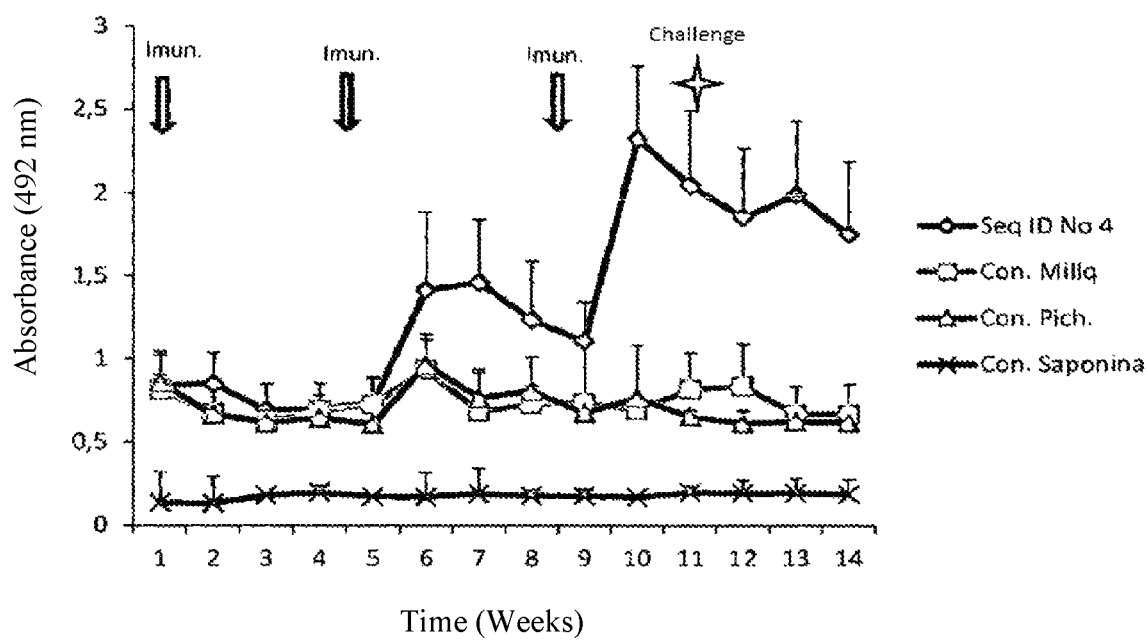
FIG. 2—Kinetics of antibodies in animals immunized with SEQ ID NO. 4. The arrows indicate inoculation and the star the time of challenge with larvae of *Rhipicephalus* (*B.*) *microplus*. The T bars indicate the difference by the adding of a standard deviation.

In weighing the ratio larvae/gram eggs, it was observed that there was no statistically significant difference between the different control groups, however when comparing these results with those obtained in groups of animals immunized with the recombinant peptides SEQ ID NO: 4, SEQ ID NO: 3 there was a decrease in weight ratio, with a statistically significant difference; between the groups of animals immunized the ratio was lower in the animals immunized with the recombinant peptide SEQ ID NO: 3 showing statistically significant difference between the groups immunized. When comparing the percentage factors of decreased egg weight, the amount of teleoginae, and the reduced fertility, one concludes that recombinant peptides obtained from the sequences described achieved a significant level of reduction and efficiency. The kinetics of recombinant anti-peptides antibody (IgG) is presented as a typical IgG immune response produced by integrating a protein used as antigen and these results are shown in FIGS. 1 and 2.

The recombinant peptides SEQ ID NO: 3 and SEQ ID NO: 4, when inoculated on bovines, do not cause any discomfort or adverse reaction in the inoculated animals.

CONCLUSION

A vaccine for *Rhipicephalus* (B.) *microplus* tick control based on recombinant peptides obtained from the sequences described has advantages because the developed vaccine is a flock vaccine in which the vaccination of the herd for three annual cycles decreases the tick population, which leads to minimization of losses already mentioned, and avoid the use of 19 or 20 baths of acaricide as it is currently being done in many farms of the country.

This invention has high social and environmental impact because currently there is the need to meet consumer demands for food free of chemicals, protection of the environment, and consequently the wild animals. Thus, in a market where the products to combat ectoparasites are mainly chemicals, it is necessary to invest in research and manufacture of alternative products for the control of these agents.

The vaccines are safe, have a good interface with the environment, and are more readily accepted by consumers, perhaps by the familiarity they have with the vaccine used in human medicine. With its use, there is a greater increase in animal production and productivity than with the use of other medications.

Unlike vaccines, the chemicals used today for combating ticks are highly toxic. If the cattle is treated with acaricide and the grace period is not respected, meat and milk should not be intended for human consumption because they are subject to the risk of poisoning, which, for prolonged periods, can lead to harmful effects on human being.

The production method of recombinant peptides used as vaccine is easier to industrial level, allows complete reproducibility on a large scale, and is more economical for low-cost production at the industrial level.

The invention claimed is:

1. A nucleotide sequence selected from the group comprising SEQ ID NO: 2, wherein said nucleotide sequences encode one or more peptides for expression in *Pichia pastoris*.

* * * * *